United States Patent [19]

Christiansen

[11] Patent Number: 5,162,498

[45] Date of Patent: Nov. 10, 1992

[54] SYNTHETIC YEAST LEADER PEPTIDES

[75] Inventor: Lars Christiansen, Lynby, Denmark

[73] Assignee: Novo Nordisk A/S, Bagsvaerd, Denmark

[21] Appl. No.: 406,392

[22] Filed: Sep. 12, 1989

Related U.S. Application Data

[63] Continuation of PCT/DK88/00147, Sep. 6, 1988.

[30] Foreign Application Priority Data

Sep. 7, 1987 [DK] Denmark .............................. 4638/87

[51] Int. Cl.$^5$ ............................................... C07K 7/10
[52] U.S. Cl. .................................... 530/324; 435/69.9
[58] Field of Search ................................ 530/324-326; 435/69.9

[56] References Cited

U.S. PATENT DOCUMENTS 4,546,082 10/1985 Kurjan .............................. 435/172.3

FOREIGN PATENT DOCUMENTS 0163529 12/1985 European Pat. Off. .
0206783 12/1986 European Pat. Off. .
8902463 3/1989 PCT Int'l Appl. .

OTHER PUBLICATIONS

Chem. Abs., vol. 103, Abs. No. 117421z, (1985).
Egel-Mitani et al., Nucleic Acids Research, vol. 15, No. 15, pp. 6303-6304 (1987).
Egel-Mitani et al., Gene, vol. 73, pp. 113-120 (1988).
Kaiser et al., Science, vol. 235, pp. 312-317 (1987).
Andrews et al., J. Biol. Chem., vol. 263, No. 30, pp. 15791-15798 (1988).
Duffaud et al., J. Biol. Chem., vol. 263, No. 21, pp. 10224-10228 (1988).

Primary Examiner—David L. Lacey
Assistant Examiner—Nina Ossanna
Attorney, Agent, or Firm—Steve T. Zelson

[57] ABSTRACT

Synthetic yeast leader peptides are disclosed which aid in extracellular secretion of heterologous proteins made recombinantly in yeast.

7 Claims, 15 Drawing Sheets

FIG. I

```
                12           24           36           48           60
       AATTCCATTCAA GAATAGTTCAAA CAAGAAGATTAC AAACTATCAATT TCATACACAATA 72           84           96          108          120
       TAAACGATTAAA AGAATGAGATTT CCTTCTATTTTT ACTGCTGTTTTA TTCGCTGCTTCC
                       M   R   F   P   S   I   F   T   A   V   L   F   A   A   S 132          144          156          168          180
       TCCGCTTTAGCT GCTCCAGTCAAC ACTACCACTGAA GATGAAACGGCT CAAATTCCAGCT
        S   A   L   A   A   P   V   N   T   T   T   E   D   E   T   A   Q   I   P   A 192          204          216          228          240
       GAAGCTGTCATC GGTTACTCTGAT TTAGAAGGTGAT TTCGATGTTGCT GTTTTGCCATTT
        E   A   V   I   G   Y   S   D   L   E   G   D   F   D   V   A   V   L   P   F 252          264          276          288          300
       TCCAACTCCACC AATAACGGTTTA TTGTTTATCAAT ACTACTATTGCC TCCATTGCTGCT
        S   N   S   T   N   N   G   L   L   F   I   N   T   T   I   A   S   I   A   A 312          324          336          348          360
       AAAGAAGAAGGT GTTTCTTTGGAT AAAAGATTCGTT AACCAACACTTG TGCGGTTCCCAC
        K   E   E   G   V   S   L   D   K   R   F   V   N   Q   H   L   C   G   S   H 372          384          396          408          420
       TTGGTTGAAGCT TTGTACTTGGTT TGCGGTGAAAGA GGTTTCTTCTAC ACTCCTAAGGCT
        L   V   E   A   L   Y   L   V   C   G   E   R   G   F   F   Y   T   P   K   A 432          444          456          468          480
       GCTAAGGGTATT GTCGAACAATGC TGTACCTCCATC TGCTCCTTGTAC CAATTGGAAAAC
        A   K   G   I   V   E   Q   C   C   T   S   I   C   S   L   Y   Q   L   E   N 492          504          516          528          540
       TACTGCAACTAG ACGCAGCCCGCA GGCTCTAGA
        Y   C   N   |
```

FIG. 7

```
                  12           24           36           48           60
         AATTCCATTCAA GAATAGTTCAAA CAAGAAGATTAC AAACTATCAATT TCATACACAATA 72           84           96          108          120
         TAAACGATTAAA AGAATGAGATTT CCTTCTATTTTT ACTGCTGTTTTA TTCGCTGCTTCC
                           M  R  F   P  S  I  F   T  A  V  L   F  A  A  S 132          144          156          168          180
         TCCGCTTTAGCT GCTCCAGTCACC GGTGACGAAAGC TTCGTCGAAATT CCAGCTGAAAAC
         S  A  L  A   A  P  V  T   G  D  E  S   F  V  E  I   P  A  E  N 192          204          216          228          240
         ACCACTTTGGCT AAGAGATTCGTT AACCAACACTTG TGCGGTTCCCAC TTGGTTGAAGCT
         T  T  L  A   K  R  F  V   N  Q  H  L   C  G  S  H   L  V  E  A 252          264          276          288          300
         TTGTACTTGGTT TGCGGTGAAAGA GGTTTCTTCTAC ACTCCTAAGGCT GCTAAGGGTATT
         L  Y  L  V   C  G  E  R   G  F  F  Y   T  P  K  A   A  K  G  I 312          324          336          348          360
         GTCGAACAATGC TGTACCTCCATC TGCTCCTTGTAC CAATTGGAAAAC TACTGCAACTAG
         V  E  Q  C   C  T  S  I   C  S  L  Y   Q  L  E  N   Y  C  N  |

372          384          396          408          420
         ACGCAGCCCGCA GGCTCTAGA
```

FIG. 8

```
                12           24             36            48           60
       AATTCCATTCAA GAATAGTTCAAA CAAGAAGATTAC AAACTATCAATT TCATACACAATA 72            84            96           108           120
       TAAACGATTAAA AGAATGAGATTT CCTTCTATTTTT ACTGCTGTTTTA TTCGCTGCTTCC
                      M  R  F    P  S  I  F  T  A  V  L   F  A  A  S 132           144           156           168           180
       TCCGCTTTAGCT GCTCCAGTTACT GGCGATGAATCA TCTGTTGAGATT CCGGAAGAGTCT
        S  A  L  A  A  P  V  T   G  D  E  S   S  V  E  I   P  E  E  S 192           204           216           228           240
       CTGATCGGTTTC TTGGATTTAGCA GGTGATGATATC GCTGAAAACACC ACTTTGGCTAAG
        L  I  G  F  L  D  L  A   G  D  D  I   A  E  N  T   T  L  A  K 252           264           276           288           300
       AGATTCGTTAAC CAACACTTGTGC GGTTCCCACTTG GTTGAAGCTTTG TACTTGGTTTGC
        R  F  V  N  Q  H  L  C   G  S  H  L   V  E  A  L   Y  L  V  C 312           324           336           348           360
       GGTGAAAGAGGT TTCTTCTACACT CCTAAGGCTGCT AAGGGTATTGTC GAACAATGCTGT
        G  E  R  G  F  F  Y  T   P  K  A  A   K  G  I  V   E  Q  C  C 372           384           396           408           420
       ACCTCCATCTGC TCCTTGTACCAA TTGGAAAACTAC TGCAACTAGACG CAGCCCGCAGGC
        T  S  I  C  S  L  Y  Q   L  E  N  Y   C  N  |

432           444           456           468           480
       TCTAGA
```

FIG. 9

```
              12           24           36           48           60
     AATTCCATTCAA GAATAGTTCAAA CAAGAAGATTAC AAACTATCAATT TCATACACAATA 72           84           96          108          120
     TAAACGATTAAA AGAATGAGATTT CCTTCTATTTTT ACTGCTGTTTTA TTCGCTGCTTCC
                   M   R   F   P   S   I   F   T   A   V   L   F   A   A   S 132          144          156          168          180
     TCCGCTTTAGCT GCTCCAGTTACT GGCGATGAATCA TCTGTTGAGATT CCGGAAGAGTCT
     S   A   L   A   A   P   V   T   G   D   E   S   S   V   E   I   P   E   E   S 192          204          216          228          240
     CTGATCATCGCT GAAAACACCACT TTGGCTAAGAGA TTCGTTAACCAA CACTTGTGCGGT
     L   I   I   A   E   N   T   T   L   A   K   R   F   V   N   Q   H   L   C   G 252          264          276          288          300
     TCCCACTTGGTT GAAGCTTTGTAC TTGGTTTGCGGT GAAAGAGGTTTC TTCTACACTCCT
     S   H   L   V   E   A   L   Y   L   V   C   G   E   R   G   F   F   Y   T   P 312          324          336          348          360
     AAGGCTGCTAAG GGTATTGTCGAA CAATGCTGTACC TCCATCTGCTCC TTGTACCAATTG
     K   A   A   K   G   I   V   E   Q   C   C   T   S   I   C   S   L   Y   Q   L 372          384          396          408          420
     GAAAACTACTGC AACTAGACGCAG CCCGCAGGCTCT AGA
     E   N   Y   C   N   |
```

FIG. 10

```
                 12           24           36           48           60
         AATTCCATTCAA GAATAGTTCAAA CAAGAAGATTAC AAACTATCAATT TCATACACAATA 72           84           96          108          120
         TAAACGATTAAA AGAATGAGATTT CCTTCTATTTTT ACTGCTGTTTTA TTCGCTGCTTCC
                         M  R  F   P  S  I  F   T  A  V  L   F  A  A  S 132          144          156          168          180
         TCCGCTTTAGCT GCTCCAGTTACT GGCGATGAATCA TCTGTTGAGATT CCGATCGCTGAA
          S  A  L  A   A  P  V  T   G  D  E  S   S  V  E  I   P  I  A  E 192          204          216          228          240
         AACACCACTTTG GCTAAGAGATTC GTTAACCAACAC TTGTGCGGTTCC CACTTGGTTGAA
          N  T  T  L   A  K  R  F   V  N  Q  H   L  C  G  S   H  L  V  E 252          264          276          288          300
         GCTTTGTACTTG GTTTGCGGTGAA AGAGGTTTCTTC TACACTCCTAAG GCTGCTAAGGGT
          A  L  Y  L   V  C  G  E   R  G  F  F   Y  T  P  K   A  A  K  G 312          324          336          348          360
         ATTGTCGAACAA TGCTGTACCTCC ATCTGCTCCTTG TACCAATTGGAA AACTACTGCAAC
          I  V  E  Q   C  C  T  S   I  C  S  L   Y  Q  L  E   N  Y  C  N 372          384          396          408          420
         TAGACGCAGCCC GCAGGCTCTAGA
          |
```

FIG. 11

```
              12           24           36           48           60
AATTC CATTCAA GAATAGTTCAAA CAAGAAGATTAC AAACTATCAATT TCATACACAATA 72           84           96          108          120
TAAACGATTAAA AGAATGAGATTT CCTTCTATTTTT ACTGCTGTTTTA TTCGCTGCTTCC
                       M  R  F      P  S  I  F   T  A  V  L    F  A  A  S 132          144          156          168          180
TCCGCTTTAGCT GCTCCAGTTACT GGCGATGAATCA TCTGTTGAGATT CCGGAAGAGTCT
 S  A  L  A   A  P  V  T   G  D  E  S   S  V  E  I   P  E  E  S 192          204          216          228          240
CTGATCATCGCT GAAAACACCACT TTGGCTAACGTC GCCATGGCTAAG AGATTCGTTAAC
 L  I  I  A   E  N  T  T   L  A  N  V   A  M  A  K   R  F  V  N 252          264          276          288          300
CAACACTTGTGC GGTTCCCACTTG GTTGAAGCTTTG TACTTGGTTTGC GGTGAAAGAGGT
 Q  H  L  C   G  S  H  L   V  E  A  L   Y  L  V  C   G  E  R  G 312          324          336          348          360
TTCTTCTACACT CCTAAGGCTGCT AAGGGTATTGTC GAACAATGCTGT ACCTCCATCTGC
 F  F  Y  T   P  K  A  A   K  G  I  V   E  Q  C  C   T  S  I  C 372          384          396          408          420
TCCTTGTACCAA TTGGAAAACTAC TGCAACTAGACG CAGCCCGCAGGC TCTAGA
 S  L  Y  Q   L  E  N  Y   C  N  |
```

FIG. 12

```
            12           24           36           48           60
   AATTCCATTCAA GAATAGTTCAAA CAAGAAGATTAC AAACTATCAATT TCATACACAATA 72           84           96          108          120
   TAAACGATTAAA AGAATGAAGGCT GTTTTCTTGGTT TTGTCCTTGATC GGATTGTGCTGG
                     M  K  A   V  F  L  V   L  S  L  I   G  L  C  W 132          144          156          168          180
   GCCCAACCAGTT ACTGGCGATGAA TCATCTGTTGAG ATTCCGGAAGAG TCTCTGATCATC
    A  Q  P  V   T  G  D  E   S  S  V  E   I  P  E  E   S  L  I  I 192          204          216          228          240
   GCTGAAAACACC ACTTTGGCTAAC GTCGCCATGGCT AAGAGATTCGTT AACCAACACTTG
    A  E  N  T   T  L  A  N   V  A  M  A   K  R  F  V   N  Q  H  L 252          264          276          288          300
   TGCGGTTCCAC TTGGTTGAAGCT TTGTACTTGGTT TGCGGTGAAAGA GGTTTCTTCTAC
    C  G  S  H   L  V  E  A   L  Y  L  V   C  G  E  R   G  F  F  Y 312          324          336          348          360
   ACTCCTAAGGCT GCTAAGGGTATT GTCGAACAATGC TGTACCTCCATC TGCTCCTTGTAC
    T  P  K  A   A  K  G  I   V  E  Q  C   C  T  S  I   C  S  L  Y 372          384          396          408          420
   CAATTGGAAAAC TACTGCAACTAG ACGCAGCCCGCA GGCTCTAGA
    Q  L  E  N   Y  C  N  |
```

FIG. 13

SYNTHETIC YEAST LEADER PEPTIDES

This application is a continuation of PCT/DK88/00147, filed Sept. 6, 1988.

The present invention relates to synthetic yeast leader peptides, DNA-sequences encoding such leader petides, vectors and transformed yeast strains.

BACKGROUND OF THE INVENTION

Yeast organisms produce a number of proteins synthesized intracellularly, but having a function outside the cell. Such extra-cellular proteins are referred to as secreted proteins. These secreted proteins are expressed initially inside the cell in a precursor or a pre-protein form containing a presequence ensuring effective direction of the expressed product across the membrane of the endoplasmatic reticulum (ER). The presequence, normally named a signal peptide, is generally cleaved off from the desired product during translocation. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer, S. R. and Rothman, J. E. Ann. Rev. Biochem. 56 (1987) 829-852).

Several approaches have been suggested for the expression and secretion in yeast of proteins heterologous to yeast. European published patent application No. 0088632A describes a process by which proteins heterologous to yeast are expressed, processed and secreted by transforming a yeast organism with an expression vehicle harbouring DNA encoding the desired protein and a signal peptide, preparing a culture of the transformed organism, growing the culture and recovering the protein from the culture medium. The signal peptide may be the desired proteins own signal peptide, a heterologous signal peptide or a hybrid of native and heterologous signal peptide.

A problem encountered with the use of signal peptides heterologous to yeast might be that the heterologous signal peptide does not ensure efficient translocation and/or cleavage after the signal peptide.

The S. cerevisiae MFα (α-factor) is synthesized as a prepro form of 165 amino acids comprising a 19 amino acid long signal- or prepeptide followed by a 64 amino acid long "leader-" or propeptide, encompassing three N-linked glycosylation sites followed by (LysArg-(Asp/Glu, Ala)$_{2-3}$αfactor)$_4$ (Kurjan, J. and Herskowitz, I. Cell 30 (1982) 933-943). The signal-leader part of the preproMFα has been widely applied to obtain synthesis and secretion of heterologous proteins in S. cerevisiae.

Use of signal/leader peptides homologous to yeast is known from a. o. U.S. Pat. No. 4,546,082, European published patent applications Nos. 011620A, 0123294A, 0123544A, 0163529A, and 0123289A and DK patent specifications Nos. 2484/84 and 3614/83.

In EP 0123289A utilization of the S. cerevisiae a-factor precursor is described whereas DK 2484/84 describes utilization of the Saccharomyces cerevisiae invertase signal peptide and DK 3614/83 utilization of the Saccharomyces cerevisiae PH05 signal peptide for secretion of foreign proteins.

U.S. Pat. No. 4,546,082, EP 0016201A, 0123294A, 0123544A, and 0163529A describe processes by which the α-factor signal-leader from Saccharomyces cerevisiae (MFα1 or MFα2) is utilized in the secretion process of expressed heterologous proteins in yeast. By fusing a DNA-sequence encoding the S. cerevisiae MFα signal/-leader sequence to the 5'end of the gene for the desired protein secretion and processing of the desired protein was demonstrated.

A number of secreted proteins are routed so as to be exposed to a proteolytic processing system which can cleave the peptide bond at the carboxy end of two consecutive basic amino acids. This enzymatic activity is in S. cerevisiae encoded by the KEX 2 gene (Julius, D. A. et al., Cell 37 (1984b), 1075). Processing of the product by the KEX 2 gene product is needed for the secretion of active S. cerevisiae mating factor α (MFα or α-factor) but is not involved in the secretion of active S. cerevisiae mating factor a.

The growing evidence for secretion being a default route in the localization of proteins in eucaryotes, where conformation of the protein to be secreted or its precursor is the essential parameter for the efficiency of the process (Pfeffer, S. R. and Rothman, J. E., Ann. Rev.Biochem. 56 (1987) 829-852), elicited a search for more efficient leaders than the MFα leader for secretion in S. cerevisiae.

Accordingly it is an object of the present invention to provide more efficient leaders than the α-factor leader for the secretion in yeast of small proteins.

In competition experiments of the type described by M. Egel-Mitani et al., GENE (1988) (in press) with insulin precursors of the type described in EP-patent application No. 163,529 we found a limiting factor in expression and secretion of the insulin precursors to be caused by the N-terminal of the precursor, most likely due to inefficient processing at the lysine-arginine sequence separating the signal-leader from insulin precursor.

A further object of the present invention is to provide a secretion system for heterologous proteins in yeast ensuring a highly efficient processing of the mature protein by means of a KEX 2 encoded endopeptidase at a dibasic sequence thus improving the yield of the mature product.

BRIEF DESCRIPTION OF THE INVENTION

According to a first aspect of the present invention there are provided a novel synthetic leader peptide having the following formula (I)

$$X_1-Pro-Val-Thr-Gly-Asp-Glu-Ser-Ser-Val-Glu-Ile-Pro- \quad (I)$$
$$(Glu-Glu-Ser-Leu-Ile)_n-X_2-Ala-Glu-Asn-Thr-Thr-Leu-$$
$$Ala-X_3-X_4-X_5$$

wherein
$X_1$ is Ala or Gln;
$X_2$ is Ile, a peptide chain with up to 10 amino acid residues, or a peptide bond;
$X_3$ is a peptide chain with up to 5 amino acid residues or a peptide bond,
$X_4$ and $X_5$ are Lys or Arg; and
n is 1 or 0.

Examples of leader peptides according to the present inventions are the following Ala—Pro—Val—Thr—Gly—Asp—Glu—Ser—Ser—Val—Glu—Ile—Pro—Glu—
Glu—Ser—Leu—Ile—Gly—Phe—Leu—Asp—Leu—Ala—Gly—Glu—Glu—Ile—
Ala—Glu—Asn—Thr—Thr—Leu—Ala—Lys—Arg Ala—Pro—Val—Thr—Gly—Asp—Glu—Ser—Ser—Val—Glu—Ile—Pro—
Glu—Glu—Ser—Leu—Ile—Ile—Ala—Glu—Asn—Thr—Thr—Leu—Ala—
Lys—Arg Ala—Pro—Val—Thr—Gly—Asp—Glu—Ser—Ser—Val—Glu—Ile—Pro—Ile—
Ala—Glu—Asn—Thr—Thr—Leu—Ala—Lys—Arg Ala—Pro—Val—Thr—Gly—Asp—Glu—Ser—Ser—Val—Glu—Ile—Pro—
Glu—Glu—Ser—Leu—Ile—Ile—Ala—Glu—Asn—Thr—Thr—Leu—Ala—
Asn—Val—Ala—Met—Ala—Lys—Arg and Gln—Pro—Val—Thr—Gly—Asp—Glu—Ser—Ser—Val—Glu—Ile—Pro—Glu—
Glu—Ser—Leu—Ile—Ile—Ala—Glu—Asn—Thr—Thr—Leu—Ala—Asn—Val—
Ala—Met—Ala—Lys—Arg According to a second aspect of the present invention there is provided DNA-sequences encoding leader peptides with the above formula (I).

Examples of such DNA-sequences are shown in FIGS. 8-10.

According to a third aspect of the present invention there is provided a replicable yeast vector containing a DNA-sequence encoding a leader petide with the above formula (I) positioned upstream to a DNA-sequence encoding the desired product and operably connected with suitable promoter and signal sequences.

The promoter may be any DNA-sequence that shows transsscriptional activity in yeast and may be derived from genes encoding proteins either homologous or heterologous to yeast. The promoter is preferably derived from a gene encoding a protein homologous to yeast. Examples of suitable promoter is the *Saccharomyces cerevisiae* MFα1 promoter. Other suitable promoters may be *S. cerevisiae* TPI, ADH or PGK promoters.

The vector according to the present invention will normally contain a signal peptide sequence positioned upstream to the DNA-sequence encoding the above leader peptide (I). The signal peptide may be any signal peptide ensuring effective direction of the expressed product into the secretory pathway of the cell. The signal peptide may be a naturally occuring signal peptide or functional parts thereof or a synthetic peptide. Suitable signal peptides have shown to be the α-factor signal peptide, the signal peptide from mouse salivary amylase or a modified carboxypeptidase signal. The mouse salivary amylase signal sequence is described by O. Hagenbüchle et al., Nature (1981) 289, 643–646. The carboxypeptidase signal is described by L. A. Valls et al., Cell 48 (1987) 887–897.

Genes encoding the desired product and the signal/-leader sequence are combined with fragments coding for a promoter, e.g. the TPI promoter ($P_{TPI}$), and a terminator, e.g. the TPI terminator ($T_{TPI}$) (T. Alber and G. Kawasaki: Nucleotide Sequence of the Triose Phosphat Isomerase Gene of *Saccharomyces cerevisiae* J.Mol.Applied Genet 1 (1982) 419–434).

The expression plasmids will further comprise the yeast 2μ replication genes REP1-3 and origin of replication and one or more selectable markers, e.g. the *Saccharomyces pombe* TPI gene as described in EP patent application No. 85303702.6.

The procedures used for ligation of the DNA sequences encoding the signal and/or leader peptide according to the invention, the promoter and terminator sequences and insertion in suitable yeast plasmids containing the necessary information for yeast replication are all well known procedures within this field of the art.

According to a fourth aspect of the present invention there is provided yeast strains being transformed with a vector according to the present invention.

According to a fifth aspect of the present invention there is provided a method for producing proteins in yeast by which a yeast strain transformed with a vector containing a DNA-sequence encoding a leader petide with the above formula (I) positioned upstream to a DNA-sequence encoding the desired product and operably connected with suitable promoter and signal sequences is cultured in a suitable medium whereupon the secreted product is isolated from the culture medium.

The yeast organism used in the process according to the present invention may be any suitable yeast organism which produces high amounts of the desired protein. Preferred yeast organisms are *Saccharomyces cerevisiae* and *Saccharomyces kluyveri*, although other yeast organisms may be used, e.g. *Schizosaccharomyces pombe* and *Saccharomyces uvarum*.

The method according to the present invention allows production of many different proteins or polypeptides in yeast. Examples of such compounds are human insulin precursors, insulin analogue precursors as described in EP patent application No. 163,529, 194,864 and 214,826 and glucagon and aprotinin.

According to one embodiment of the present invention a DNA-sequence encoding a leader peptide with the above formula (I) will be connected directly to the gene for the desired product. During secretion the leader peptide will be cleaved off from the expressed product enabling isolation of the desired product (e.g. glucagon or aprotinin) from the culture medium without the need for further in vitro conversion.

To secure a more effective processing of the leader peptide at the C-terminal Lys-Arg residues during secretion it might be preferable to express the desired product with an additional N-terminal amino acid sequence. This additional amino acid sequence must then later on be cleaved off from the remaining part of the molecule by in vitro conversion. For the purpose of such in vitro cleavage the additional peptide chain may be provided with a selective cleavage site positioned N-terminally to the desired product. If the desired product does not contain methionine, cyanogen bromid cleavage at methionin adjacent to the desired protein would be operative. Also, contemplated is arginine—or lysine-cleavage at an arginine or lysine adjacent to the desired protein by means of trypsinlike protease.

Finally the additional peptide chain may be cleaved off in vitro by other suitable proteolytic enzymes provided that it constitutes a cleavage site for such enzymes.

As used herein the expression "proteins heterologous to yeast" means proteins not produced by the yeast organism. "Secretion" means exportation of an expressed product through the cell wall into the medium or at least past the cellular membrane. "Processing" means cellular cleavage of the signal/leader peptide from the mature protein so as to produce the heterologous protein unaccompanied by any portion of the signal/leader peptide. "Signal/leader peptide" means a preproregion ensuring direction of the expressed product into the secretory pathway of the cell and consisting of an N-terminal signal sequence of hydrophobic composition followed by a hydrophilic leader region. "Mature protein" means the protein encoded for by the DNA sequence inserted in the expression vehicle. The mature protein may be an active protein or polypeptide or a precursor thereof which is further converted into the active end product by in vitro conversion.

BRIEF DESCRIPTION OF THE DRAWINGS

The present invention is further illustrated by reference to the accompanying drawings in which:

FIG. 7 shows the DNA sequence of the EcoRI-Xba fragment of pT7αMI3 and the corresponding protein in single letter nomenclature below, FIG. 8 shows the DNA sequence of the EcoRI-XbaI fragment of pT7-178 and the corresponding protein in one letter nomenclature below, FIG. 9 shows the DNA sequence of the EcoRI-XbaI fragment of pT7-193 and the corresponding protein in one letter nomenclature below, FIG. 10 shows the DNA sequence of the EcoRI-XbaI fragment of pT7-194 and the corresponding protein in one letter nomenclature below, FIG. 11 shows the DNA sequence of the EcoRI-XbaI fragment of pT7-195 and the corresponding protein in one letter nomenclature below, FIG. 12 shows the DNA sequence of the EcoRI-XbaI fragment of pT7-200 and the corresponding protein in one letter nomenclature below, FIG. 13 shows the DNA sequence of the EcoRI-XbaI fragment encoding the signal-leader-p-insulin of pLaC212spx3 and the corresponding protein in one letter nomenclature below.

The present invention will be exemplified by the following examples showing the production of certain insulin precursors.

DETAILED DESCRIPTION

1. Plasmids and DNA materials

Figure 1:
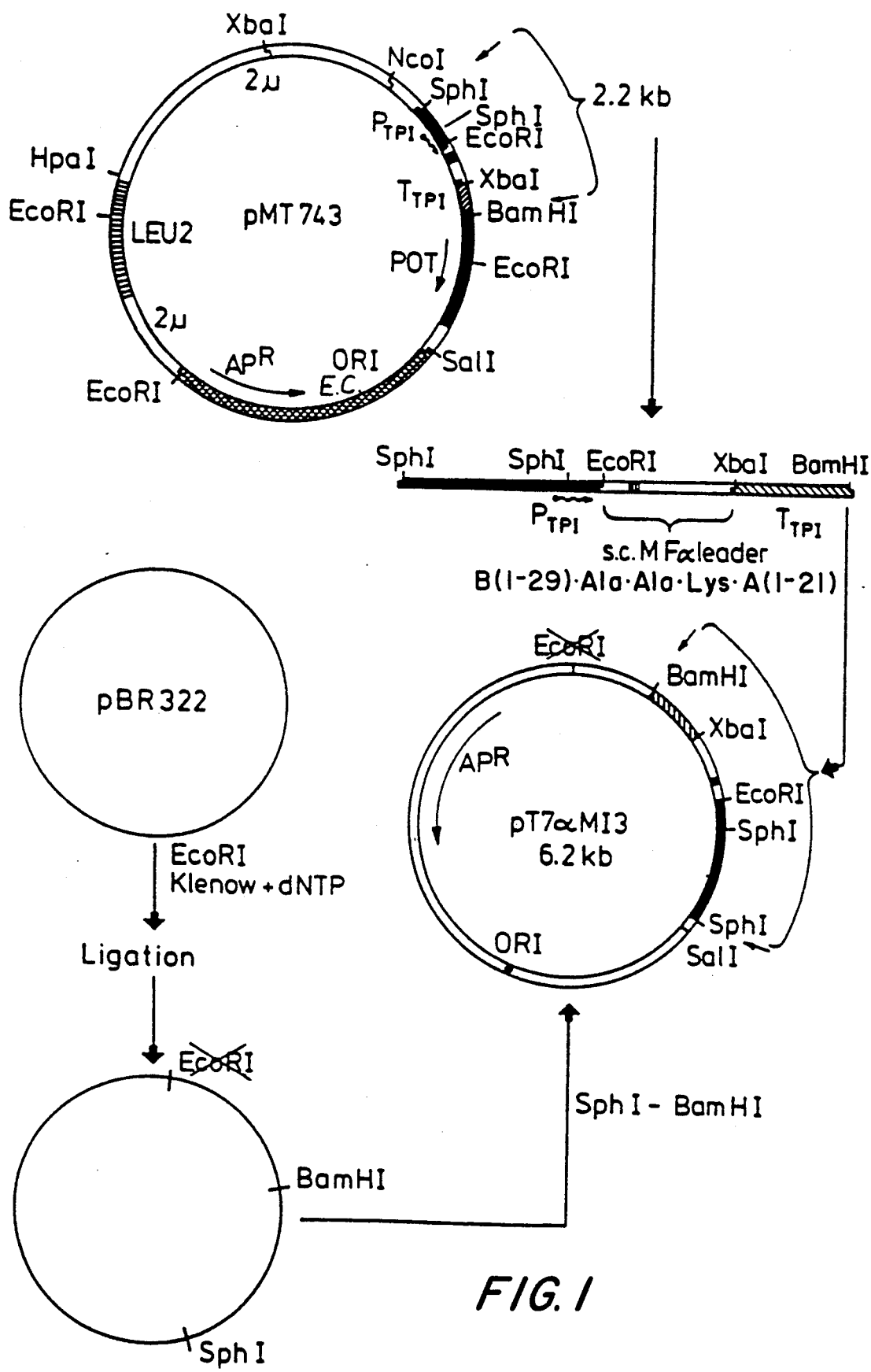
FIG. 1 shows the pMT743 plasmid and the construction of plasmid pT7αMI3.

All expression plasmids are of the C-POT type. Such plasmids are described in EP patent application No. 85303702.6 and are characterized in containing the *S. pombe* triose phosphat isomerase gene (POT) for the purpose of plasmid stabilization. A plasmid containing the POT-gene is available from a deposited *E. coli* strain (ATCC 39685). The plasmids will furthermore contain the *S. cerevisiae* triose phosphat isomerase promoter and terminator ($P_{TPI}$ and $T_{TPI}$). They are identical to pMT743 (M. Egel-Mitani et al. GENE (1988) (in press) (see FIG. 1) except for the region defined by the EcoRI-XbaI restriction site encoding a signal/leader-/insulin precursor sequence.

The assembly of the signal/leader/insulin precursor coding fragments described in this context has for practical reasons taken place in an *E. coli* plasmid pT7αMI3. This plasmid (see FIG. 1) is a pBR322 derivative in which the EcoRI site has been eliminated by religating the EcoRI cut, with Klenow polymerase and dNTP flushended plasmid, and in which the BamHI-SphI fragment has been replaced by the 2.2 kb SphI-BamHI fragment of the above pMT743. This latter fragment contains a sequence encoding an insulin precursor B(1-29)-Ala-Ala-Lys-A(1-21) linked to the MFα leader and signal and the *S. cerevisiae* triose phosphat isomerase promoter and terminator sequences (see FIG. 1). In this SpHI-Bam HI fragment the sequence encoding the signal/leader/insulin precursor is contained in the 0.5 kb EcoRI-XbaI fragment. The general principle of the construction work described in the following examples is to replace the MFα leader sequence by a leader sequence according to the present invention. The signal sequence as well as the sequence for the desired product may also be substituted. The DNA-sequence of the EcoRI-XbaI fragment of pT7αMI3 is shown in FIG. 7.

Several of the constructs further embody fragments from the *S. kluyveri* α mating pheromone gene (M. Egel-Mitani and M. Trier Hansen (1987) Nucl. Acid Res. 15, 6306).

Finally a number of synthetic DNA fragments have been applied.

The synthetic DNA-fragments were synthesized on an automatic DNA synthesizer (Applied Biosystems Model 380A) using phosphoramidite chemistry and commercially available reagents (S. L. Beaucage and M. H. Caruthers (1981) Tetrahedron Letters 22, 1859–1869). The oligonucleotides were purified by polyacryl amide gel electrophoresis under denaturating conditions.

Prior to annealing the complementary DNA single strands were kinased by T4 poly nucleotide kinase and ATP.

The fragments resulting from this procedure are the following:

NOR243/244: ACCGGTGACGAAAGCTTCGTCGA
TGGCCACTGCTTTCGAAGCAGCTTTAA

NOR512/513: AATTCCTGAGGAATCTTT
GGACTCCTTAGAAACTAG

NOR308/309: AATTGATATCG
CTATAGC

NOR245/246: CTGAAAACTCCACTTTGGCTAAGAG
GACTTTTGAGGTGAAACCGATTCTCTAA

NOR348/350: TAACGTCGCCATGGCTAAGAGATTCGTTAAC
GCAGCGGTACCGATTCTCTAAGCAATTG

NOR217/218: CAACCAGTCAC
CCGGGTTGGTCAGTGGC

All other methods used and materials are common state of the art knowledge (T. Maniatis et al. (1982) Molecular Cloning. Cold Spring Harbor Press).

The following examples 1–4 illustrate the expression and secretion of insulin precursors of the type B(1-29)-Ala-Ala-Lys-A(1-21) by means of various of the signal-leader sequences according to the present invention and example 5 illustrate the expression and secretion of an insulin precursor of the aforementioned type, but in which the amino acid residue in position B(27) has been substituted with Arg and the amino acid residue in position A(21) has been substituted with Gly. As used in the following text B(1-29) means a shortened B chain of human insulin from B(1)Phe to B(29)Lys and A(1-21) means the A chain of human insulin.

EXAMPLE 1 pLAC178 construction

The 4.5 kb SalI-XbaI fragment, the 1317 bp SalI-HincII fragment and the 333 bp EcoRI*-XbaI fragment of pT7αMI3 were joined with the synthetic fragment NOR243/244:

ACCGGTGACGAAAGCTTCGTCGA
TGGCCACTGCTTTCGAAGCAGCTTTAA resulting in pT7-172.

The 5.6 kb EcoRI-XbaI, the 172 bp EcoRI-PvuII and the 278 bp HinfI-XbaI fragments of pT7-172 were joined with the synthetic fragment NOR 245/246:

CTGAAAACACCACTTTGGCTAAGAG
GACTTTTGTGGTGAAACCGATTCTCTAA resulting in pT7-178.

Figure 2:
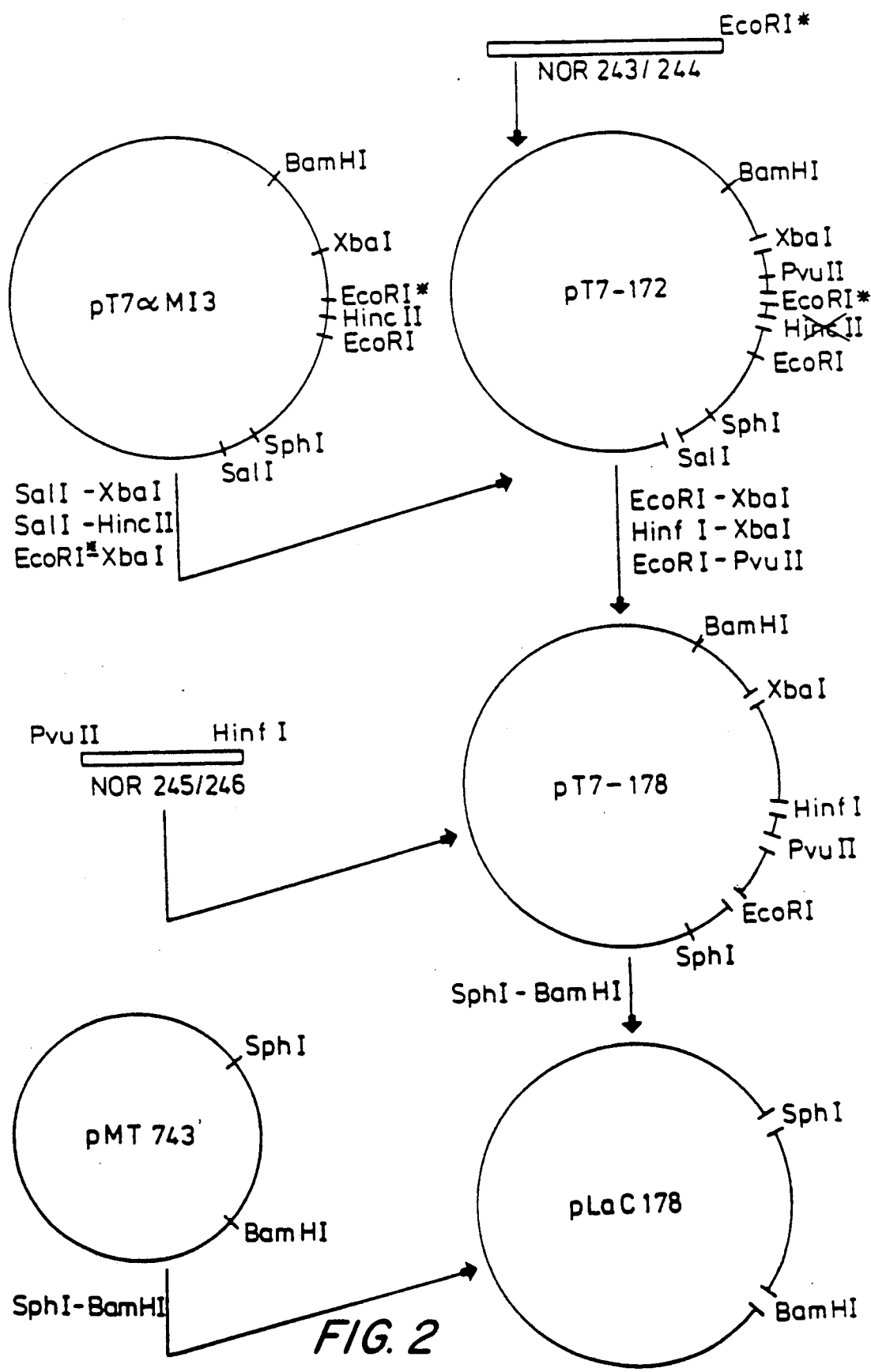
FIG. 2 illustrates the construction of plasmids pT7-178 and pLaC178.

Replacing the SphI-BamHI fragment of pMT743 with the 2.2 kb SphI-BamHI fragment of pT7-178, resulted in pLaC178. The construction of pLaC178 is illustrated in FIG. 2.

The DNA-sequence of the EcoRI-XbaI fragment of pT7-178 is shown in FIG. 8.

pLaC193–195 construction

The 5.6 kb EcoRI-XbaI and the 203 bp PvuII-XbaI fragment of pT7αMI3 were joined with the synthetic fragment NOR308/309.

AATTGATATCG
CTATAGC

From the resulting plasmid the 210 bp EcoRV-XbaI fragment was joined with the 138 bp EcoRI-MaeIII and the 5.6 kb EcoRI-XbaI fragment of pT7-178 and the below indicated fragments from the *S. kluyveri* MFα gene:

74 bp MaeIII-EcoRV resulting in pT7-193
47 bp MaeIII-Sau3A resulting in pT7-194
32 bp MaeIII-MspI resulting in pT7-195.

Figure 3:
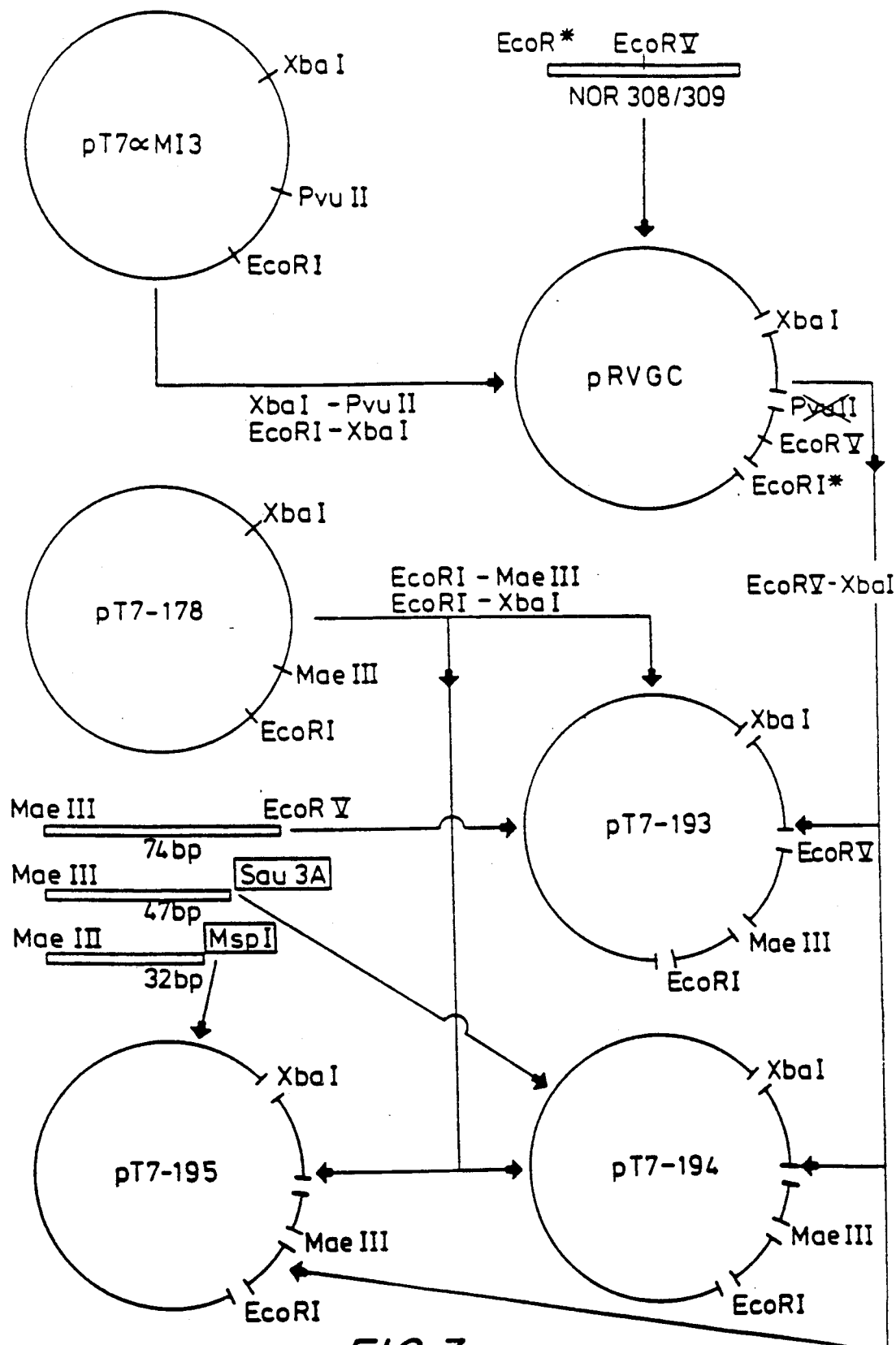
FIG. 3 illustrates the construction of plasmids pT7-193, pT7-194 and pT7-195.

The underlined restriction ends were filled in by Klenow polymerase and dNTP. The construction of these plasmids is illustrated in FIG. 3.

The replacement of the SphI-BamHI fragment of pMT743 with the SphI-BamHI fragments of the pT7-193 to 195 plasmids resulted in the plasmids pLaC193 to 195, respectively.

Plasmid pLaC193 encodes the following leader sequence:

Ala—Pro—Val—Thr—Gly—Asp—Glu—Ser—Ser—Val—Glu—Ile—Pro—Glu—
Glu—Ser—Leu—Ile—Gly—Phe—Leu—Asp—Leu—Ala—Gly—Glu—Glu—Ile—
Ala—Glu—Asn—Thr—Thr—Leu—Ala—Lys—Arg.

The signal sequence is a codon optimized *S. cerevisae* signal sequence (see Michi Egel Mitani et. al. (1988) supra). The DNA-sequence of the EcoRI-XbaI fragment of pT7-193 is shown in FIG. 9.

Plasmid pLaC194 encodes the following leader sequence:

Ala—Pro—Val—Thr—Gly—Asp—Glu—Ser—Ser—Val—Glu—Ile—Pro—Glu—
Glu—Ser—Leu—Ile—Ile—Ala—Glu—Asn—Thr—Thr—Leu—Ala—Lys—Arg.

The signal sequence is as above. The DNA-sequence of the EcoRI-XbaI fragment of pT7-194 is shown in FIG. 10.

Plasmid pLaC195 encodes the following leader sequence:

Ala—Pro—Val—Thr—Gly—Asp—Glu—Ser—Ser—Val—Glu—Ile—Pro—Ile—
Ala—Glu—Asn—Thr—Thr—Leu—Ala—Lys—Arg.

The signal sequence is as above. The DNA-sequence of the EcoRI-XbaI fragment of pT7-195 is shown in FIG. 11.

EXAMPLE 2 pLaC200 construction

Figure 4:
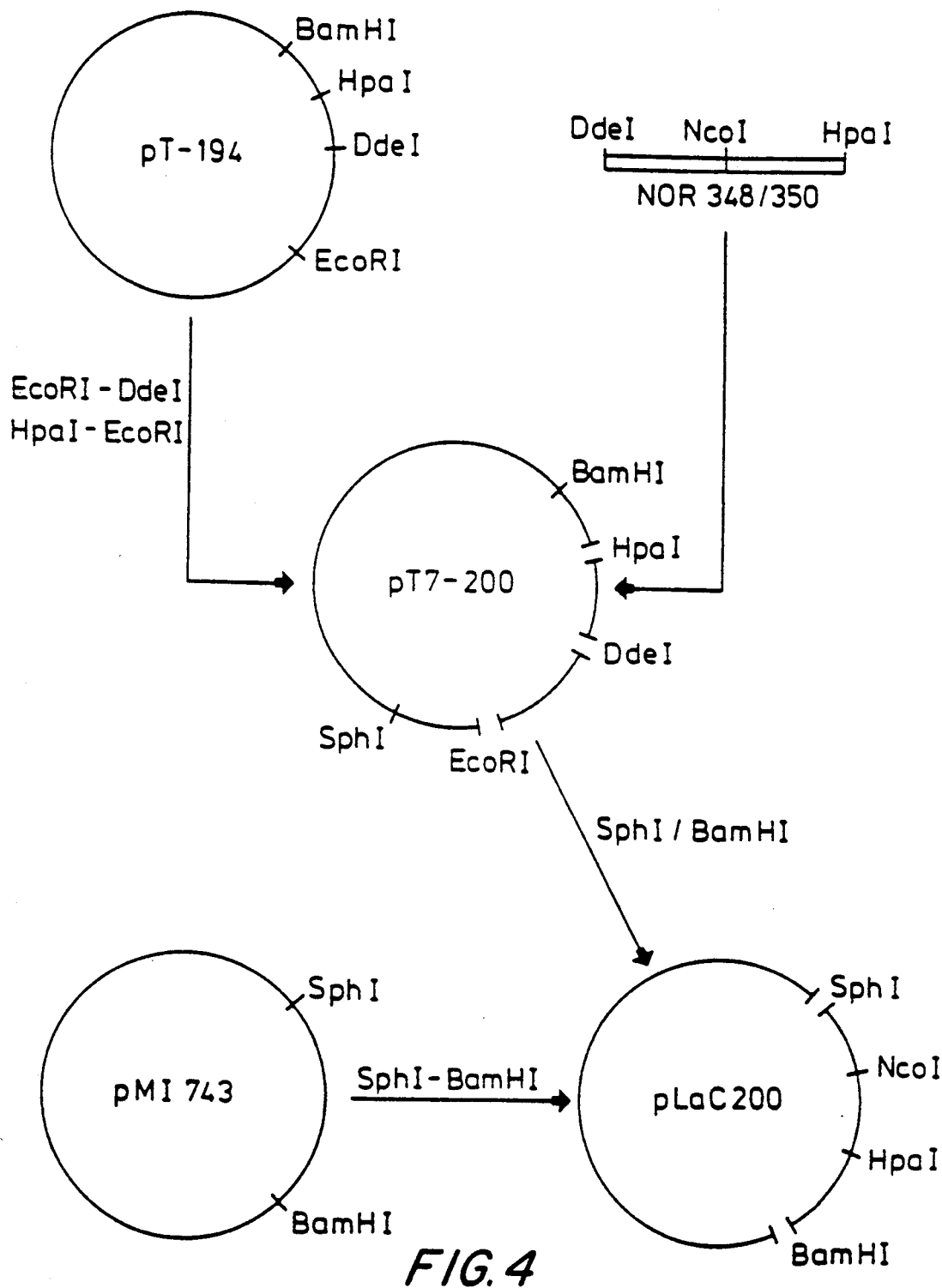
FIG. 4 illustrates the construction of plasmids pT7-200 and pLaC200.

The 213 bp EcoRI-DdeI and the 5.9 kb HpaI-EcoRI fragment of pT7-194 were joined with the synthetic fragment NOR348/350:

TAACGTCGCCATGGCTAAGAGATTCGTTAAC
GCAGCGGTACCGATTCTCTAAGCAATTG resulting in pT7-200. The replacement of the SphI-BamHI fragment in pMT743 with the 2.2 kb SphI-BamHI fragment of pT7-200 resulted in pLaC200. The construction of pLaC200 is shown in FIG. 4.

Plasmid pLaC200 encodes the following leader sequence:

Ala—Pro—Val—Thr—Gly—Asp—Glu—Ser—Ser—Val—Glu—Ile—Pro—Glu—
Glu—Ser—Leu—Ile—Ile—Ala—Glu—Asn—Thr—Thr—Leu—Ala—Asn—Val—
Ala—Met—Ala—Lys—Arg.

The signal sequence is the same as in example 1. The DNA-sequence of the EcoRI-XbaI fragment of pT7-200 is shown in FIG. 12.

EXAMPLE 3 pLaC212spx3 construction

Figure 5:
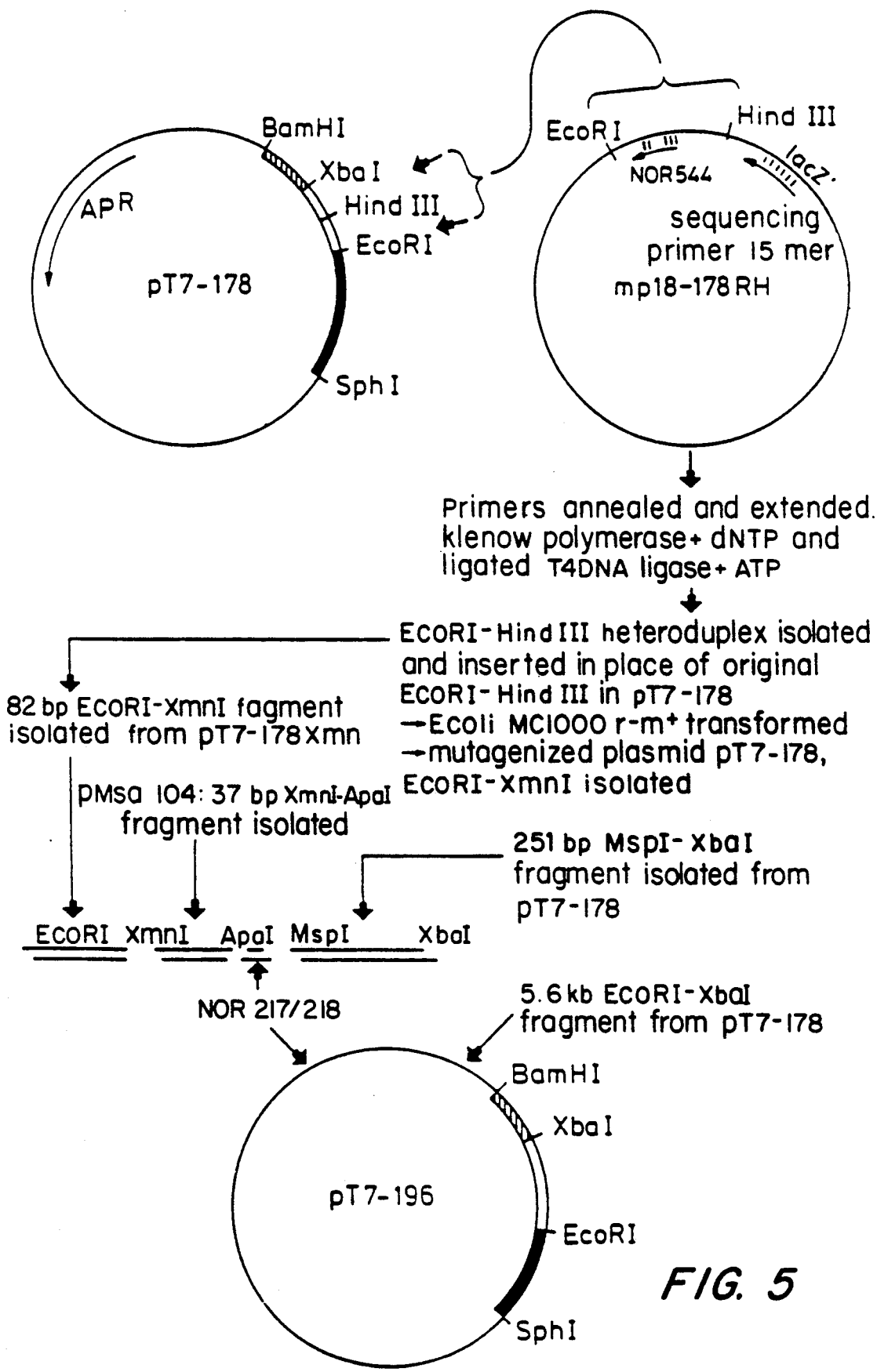
FIG. 5 illustrates the construction of plasmid pT7-196.

Plasmid pT7-178 was in vitro mutagenized by the double primer method applying the synthetic DNA NOR544:

3' CTTACTTTCAGAAGATAAAAATGACG 5' essentially as described by K. Norris et. al. (1983) Nucl. Acid Res. 11, 5103-5112 (FIG. 5).

The resulting plasmid now contains a XmnI cleavage site enabling the isolation of a 82 bp EcoRI-XmnI fragment, which together with the 37 bp XmnI-ApaI fragment from pMSA104 (O. Hagenbüchle et al. Nature (1981) 289, 643-646) encoding the mouse salivary amylase signal peptide residue three to fifteen, was joined in a ligation further including the 251 bp MspI-Xba and the 5.6 kb EcoRI-Xba fragments of pT7-178 and the synthetic DNA fragment NOR217/218:

CAACCAGTCAC
CCGGGTTGGTCAGTGGC resulting in the plasmid pT7-196 (FIG. 5) containing a modified mouse salivary signal (amino acid residues 3-15).

Replacement of the SphI-BamHI fragment of pMT743 with the 2.2 kb SphI-BamHI fragment of pT7-196, resulted in pLaC196.

Figure 6A:
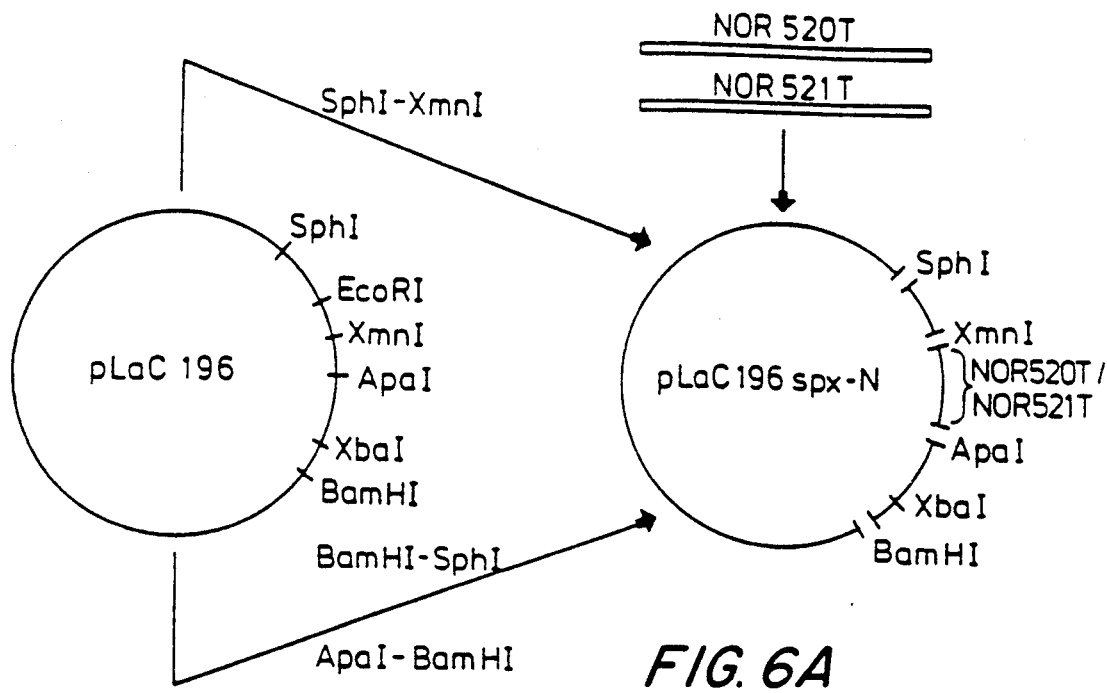
FIGS. 6A and 6B illustrate the construction of plasmid pLaC212spx3.

The modified mouse salivary amylase signal peptide was further mutagenized by replacing the XmnI-ApaI fragment of pLaC196 with the synthetic adaptors NOR520T or 521T (FIG. 6a) produced from NOR520: tcccatctgttttcttgttattgtccttgatcggattctgctGGGCCCA NOR521: tcttcttgttattgtccttgatcggattctgctGGGCCCA where the nucleotides in small letters were incorporated from pools composed of 91% of the nucleotide indicated and 3% of each of the other nucleotides. NOR520 and 521 were auto annealed (underlined 3' end), extended by klenow polymerase and dNTP, resulting in double stranded DNA fragments of 90 and 72 bp, respectively. These fragments were cleaved by ApaI and the resulting fragments NOR521T of 47 bp and NOR521T of 38 bp were purified by polyacrylamide gelelectrophoresis.

Plasmids resulting from this procedure were isolated from transformants of an E. coli strain and individually transformed into the S. cerevisiae strain MT663. The resulting yeast transformants were screened for insulin precursor secretion by colony immunoblotting with a monoclonal mouse anti insulin precursor and decorated with horsradish peroxidase conjugated rabbit anti mouse IgG. The transformants giving the strongest response were further analyzed. The best of these harboured the plasmid pLaC196spx3 in which the signal peptide was changed to:

MKAVFLVLSLIGFCWA

The exact nucleotide sequence as determined by Maxam-Gilbert sequencing from the EcoRI site towards XabI is given in FIG. 13.

The spx3 signal peptide is in the above context approximately a factor of two superior to the original signal petide of pLaC196 as estimated from secreted insulin precursor levels obtained.

Surprisingly spx3 originating from the NOR520T mutagenesis is two codon shorter than would be expected, the only explanation for this must be length heterogeneity in the original single strands of NOR520, or by a polymerase jump in the extension reaction en route to NOR520T.

Figure 6B:
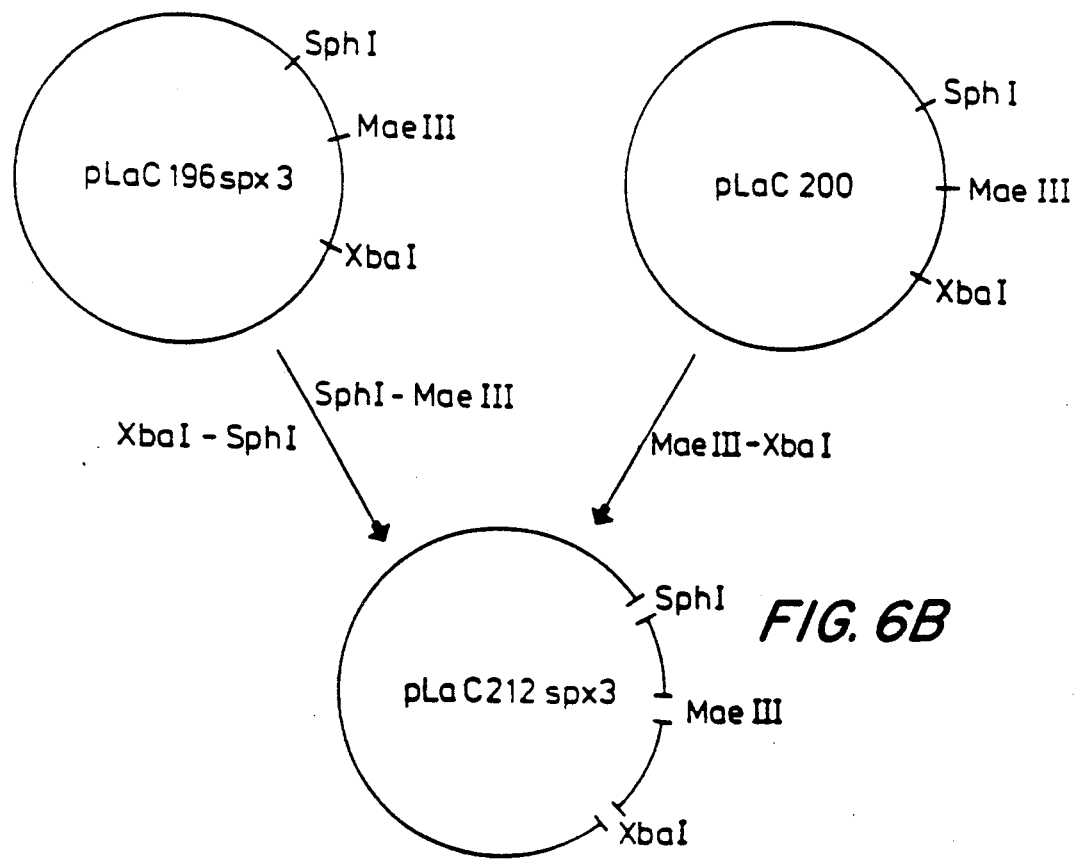

Replacement of the MaeIII-XbaI fragment, encoding the leader-insulin precursor part of pLaC196spx3 with the analogous MaeIII-XbaI fragment of pLaC200, resulted in pLaC212spx3 (FIG. 6b).

Plasmid pLaC212spx3 encodes the following leader sequence:

Gln—Pro—Val—Thr—Gly—Asp—Glu—Ser—Ser—Val—Glu—Ile—Pro—Glu—
Glu—Ser—Leu—Ile—Ile—Ala—Glu—Asn—Thr—Thr—Leu—Ala—Asn—Val—
Ala—Met—Ala—Lys—Arg.

The signal sequence is the mutated mouse salivari signal. The DNA-sequence of the EcoRI-XbaI fragment of pLaC212spx3 is shown in FIG. 13.

EXAMPLE 4

DNA encoding a precursor of an insulin analogue having Gln in position B(12), Arg in position B(27) and Gly in position A(21), respectively, was derived from plasmid pKFN126 (Markussen et al. (1987) Protein Engineering: 1, 215-223) by replacing the 90 bp StuI-XbaI fragment with the following synthetic DNA:

```
CCCAAGGCTGCTAAGGGTATTGTCGAACAATGCTGTACCTCCATCTGCTCCTTGTA
GGGTTCCGACGATTCCCATAACAGCTTGTTACGACATGGAGGTAGACGAGGAACAT

CCAATTGGAAAACTACTGCGGTTAAT
GGTTAACCTTTTGATGACGCCAATTAGATC
```

Figure 14:
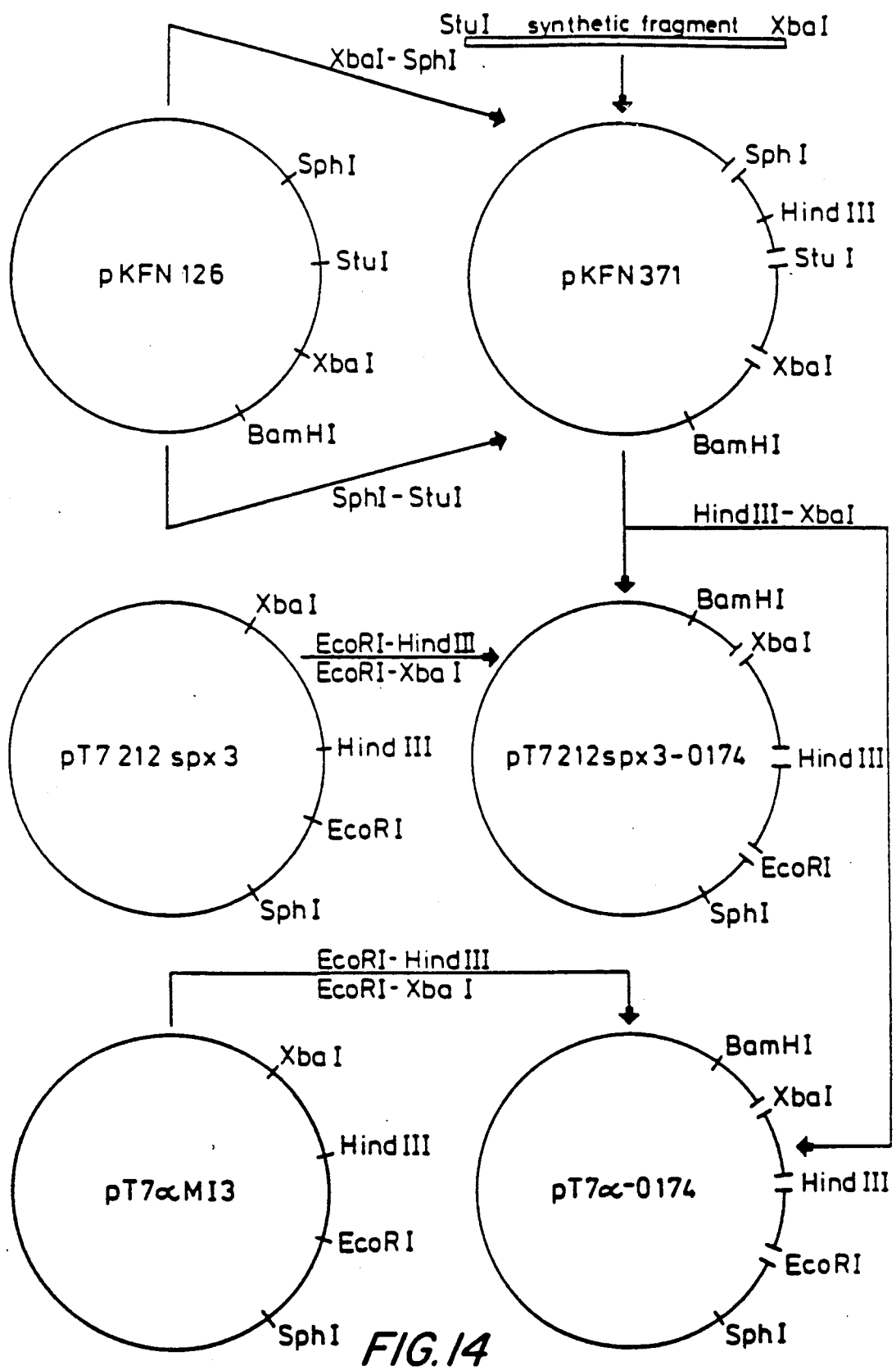
FIG. 14 illustrates the construction of plasmids pKFN371, pT7212spx-3017 and pT7α-0174
Figure 15:
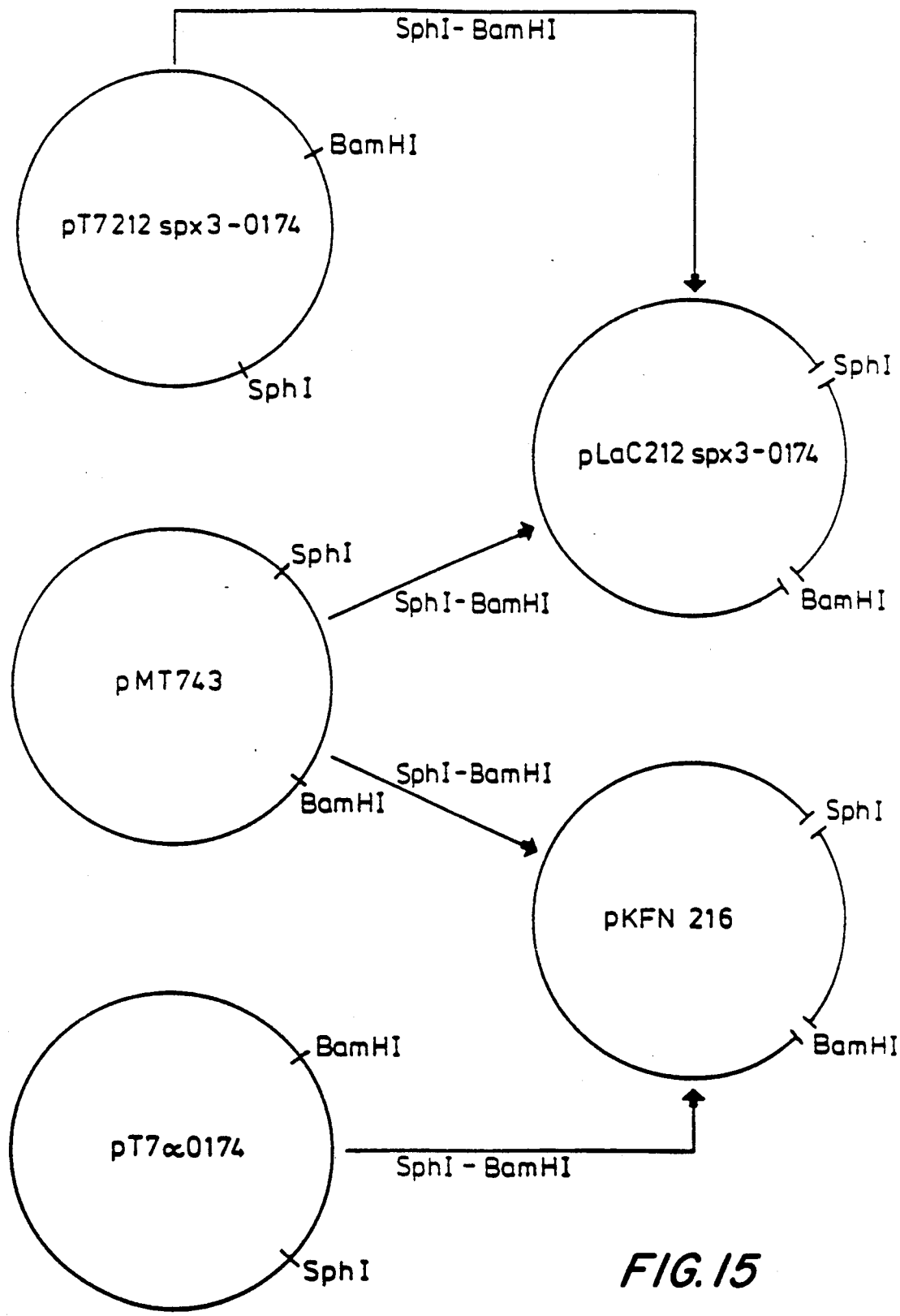
FIG. 15 illustrates the construction of plasmids pLaC212spx3-0174 and pKFN216.

From the resulting plasmid pKFN371 the 124 bp HindIII-XbaI fragment was isolated and used to replace the analogous HindIII-XbaI fragment of pT7212spx3 and pT7αMI3 (see FIG. 14). Hereby the DNA-sequence encoding the above insulin analogue was amended into a sequence coding for an insulin analogue wherein B(27) is Arg and A(21) is Gly. By replacing the SphI-BamHI fragment of pMT743 with the 2.2 kb SphI-BamHI fragment of the plasmids pT7212spx3-0174 and pT7α-0174 resulting from these constructions, pLaC212spx3-0174 and pKFN216, respectively, were constructed (see FIG. 15). In these plasmids the 212spx3 and the S. cerevisiae MFα leader, respectively, mediate the secretion of the insulin analogue.

EXAMPLE 5

Plasmids prepared as described above were transformed into S. cerevisiae strains carrying deletions in the TPI gene by selecting for growth on glucose.

The transformed yeast strain were grown on YPD medium (Sherman, F. et al., Methods in Yeast Genetics, Cold Spring Harbor Laboratory 1981). For each strain 6 individual 5 ml cultures were shaken at 30° C. until they reached an $OD_{600}$ of approx. 15 (approx. 48 hours). After centrifugation the supernatant was removed for HPLC analysis by which method the concentration of secreted insulin precursor was measured by a method as described by Leo Snel et al., (1987) Chromotographia 24, 329-332.

The expression levels of various insulin precursors are summarized in the following tables 1 and 2.

In table 1 and 2 the expression level of the insulin precursors by use of a leader sequence according to the present invention is indicated in percentage of the expression level of the same insulin precursor expressed and secreted in the same yeast strain, however by use of the MFα signal/leader sequence.

TABLE 1

Expression levels of insulin precursor B(1-29)-Ala-Ala-Lys-A(1-21) in yeast transformants.

| Plasmid | Expression level* |
|---|---|
| pMT743 | 100% |
| pLaC193 | 160% |
| pLaC194 | 200% |
| pLaC195 | 90% |
| pLaC200 | 170% |
| pLaC212spx3 | 120% |

*The expression levels are indicated in percentage of the expression level of pMT743 which is arbitrarily set to 100%.

TABLE 2

Expression levels of insulin precursors wherein B(27) is Arg and A(21) is Gly.

| Plasmid | Expression level** |
|---|---|
| pKFN216 | 100% |
| pLaC212spx3-0174 | 150% |

**The expression levels are indicated in percentage of the expression level of pKFN216 which is arbitrarily set to 100%.

I claim:

1. Leader peptide for secretion in yeast having the following formula:

$X_1$-Pro-Val-Thr-Gly-Asp-Glu-Ser-Ser-Val-Glu-Ile-Pro-Glu-Glu-Ser-Leu-Ile-$X_2$-Ala-Glu-Asn-Thr-Thr-Leu-Ala-$X_3$-$X_4$-$X_5$ wherein
$X_1$ is Ala or Gln;
$X_2$ is Ile, a peptide chain with up to 10 amino acid residues, or a peptide bond;
$X_3$ is a peptide chain with up to 5 amino acid residues or a peptide bond; and
$X_4$ and $X_5$ are Lys or Arg.

2. Leader peptide according to claim 1, wherein $X_2$ is Ile, and $X_1$, $X_3$, $X_4$ and $X_5$ are defined as in claim 1.

3. Leader peptide according to claim 1, wherein $X_2$ is the peptide chain Gly-Phe-Leu-Asp-Leu-Ala-Gly-Asp-Asp-Ile, and $X_1$, $X_3$, $X_4$ and $X_5$ are defined as in claim 1.

4. Leader peptide according to claim 1 having the following peptide sequence:

Ala—Pro—Val—Thr—Gly—Asp—Glu—Ser—Ser—Val—Glu—Ile—Pro—Glu—
Glu—Ser—Leu—Ile—Gly—Phe—Leu—Asp—Leu—Ala—Gly—Glu—Glu—Ile—
Ala—Glu—Asn—Thr—Thr—Leu—Ala—Lys—Arg.

5. Leader peptide according to claim 1 having the following paptide sequence:

Ala—Pro—Val—Thr—Gly—Asp—Glu—Ser—Ser—Val—Glu—Ile—Pro—
Glu—Glu—Ser—Leu—Ile—Ile—Ala—Glu—Asn—Thr—Thr—Leu—Ala—
Lys—Arg.

6. Leader peptide according to claim 1 having the following peptide sequence:

Ala—Pro—Val—Thr—Gly—Asp—Glu—Ser—Ser—Val—Glu—Ile—Pro—
Glu—Glu—Ser—Leu—Ile—Ile—Ala—Glu—Asn—Thr—Thr—Leu—Ala—
Asn—Val—Ala—Met—Ala—Lys—Arg.

7. Leader petide according to claim 1 having the following peptide sequence:

Gln—Pro—Val—Thr—Gly—Asp—Glu—Ser—Ser—Val—Glu—Ile—Pro—Glu—
Glu—Ser—Leu—Ile—Ile—Ala—Glu—Asn—Thr—Thr—Leu—Ala—Asn—Val—
Ala—Met—Ala—Lys—Arg.

* * * * *